United States Patent [19]

Wu et al.

[11] 4,077,959

[45] Mar. 7, 1978

[54] 10-(BIS-PYRROLINYL)ACRIDANS

[75] Inventors: Yao Hua Wu; Walter G. Lobeck, Jr., both of Evansville, Ind.

[73] Assignee: Mead Johnson & Company, Evansville, Ind.

[21] Appl. No.: 641,007

[22] Filed: Dec. 15, 1975

Related U.S. Application Data

[60] Division of Ser. No. 521,618, Nov. 6, 1974, Pat. No. 3,946,004, which is a continuation-in-part of Ser. No. 336,845, Feb. 28, 1973, abandoned, which is a continuation-in-part of Ser. No. 147,667, May 27, 1971, Pat. No. 3,719,671.

[51] Int. Cl.$^2$ ............................................. C07D 219/14
[52] U.S. Cl. ................................................. 260/279 R
[58] Field of Search ...................................... 260/279 R

[56] References Cited

U.S. PATENT DOCUMENTS

| 2,770,727 | 11/1973 | Brack | 260/240.8 |
| 3,498,986 | 3/1970 | Meisels et al. | 260/279 R |
| 3,962,252 | 6/1976 | Wu et al. | 260/279 R |

OTHER PUBLICATIONS

Moskoukina et al., Chemical Abstracts, vol. 73, 14,649n, (1970).

*Primary Examiner*—Donald G. Daus
*Assistant Examiner*—D. Rivers
*Attorney, Agent, or Firm*—Robert H. Uloth; Robert E. Carnahan

[57] ABSTRACT

Novel amidine compounds selected from the group consisting of bis-pyrrolinyl derivatives of phenothiazines, phenoxazines and acridans are obtained by reacting a phenothiazine, phenoxazine or acridan with a pyrrolidinone in the presence of phosphorus oxychloride. The phenothiazine, phenoxazine, or acridan can also be alkylated with 2-chloro-1-(1-pyrrolin-2-yl)-2-pyrroline to provide compounds of the invention. Typical examples of bis-pyrrolinyl derivatives are 2-methoxy-10-[5-methyl-1-(5-methyl-1-pyrrolin-2-yl)-2-pyrrolin-2yl]phenothiazine, 10-[1-(1-pyrrolin-2-yl)-2-pyrrolin-2-yl]phenoxazine, and 9,9-dimethyl-10-[5-methyl-1-(5-methyl-1-pyrrolin-2-yl)-2-pyrrolin-2-yl]acridan. The amidine compounds are useful as diuretics, smooth muscle relaxants and antithrombogenic agents.

4 Claims, No Drawings

10-(BIS-PYRROLINYL)ACRIDANS

CROSS-REFERENCE TO RELATED APPLICATIONS

This application is a division of copending application Ser. No. 521,618 filed Nov. 6, 1974, and now U.S. Pat. No. 3,946,004, which is a continuation-in-part of then copending application Ser. No. 336,845 filed Feb. 28, 1973, and now abandoned, which is a continuation-in-part of then copending application Ser. No. 147,667, filed May 27, 1971, now U.S. Pat. No. 3,719,671.

BACKGROUND OF THE INVENTION

This invention pertains to heterocyclic carbon compounds which have drug and bio-affecting properties. The invention is particularly concerned with amidines of the group consisting of bis-pyrrolinyl phenothiazines, bis-pyrrolinyl acridan, and bis-pyrrolinyl phenoxazines. The compounds of the invention are of value as smooth muscle relaxant, antithrombogenic and as diuretic agents. Other features of the invention are a therapeutic process for producing smooth muscle relaxant, antithrombogenic and diuretic effects in mammals by administration of the amidine compounds.

We have previously disclosed pyrrolinyl phenothiazine in our co-pending U.S. patent application Ser. No. 147,667 U.S. Pat. No. 3,719,671) as being of interest for their intestinal relaxant and antithrombogenic activity. The phenothiazine compounds of the present application are bis-pyrrolinyl phenothiazines whereas the pyrrolinyl phenothiazines of the co-pending patent application are monomeric pyrrolinyl derivatives.

SUMMARY OF THE INVENTION

This invention relates to a group of amidines represented by Formula I and non-toxic pharmaceutically acceptable acid addition salts thereof.

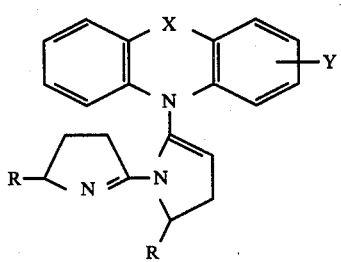

The substances of Formula I are more particularly characterized as bis-pyrrolinyl derivatives belonging to the group of amidines consisting of bis-pyrrolinyl phenothiazines, bis-pyrrolinyl acridans and bis-pyrrolinyl phenoxazines. Substances of Formula I are useful as smooth muscle relaxants, inhibitors of platelet aggregation, and as diuretic agents in mammals.

In Formula I, X is selected from the group consisting of sulfur, oxygen, or the divalent methylene radical —C($Z_1Z_2$)— wherein $Z_1$ and $Z_2$ represent independently selected hydrogen or lower straight chain alkyl of 1 to 4 carbon atoms inclusive. When X is sulfur, the compounds are 10-bis-pyrrolinyl phenothiazine derivatives. When X is oxygen, the compounds are bis-pyrrolinyl phenoxazine derivatives. When X signifies the divalent radical —C($Z_1Z_2$)—, the compounds are bis-pyrrolinyl acridan derivatives. In the foregoing formulas, Y represents hydrogen, trifluoromethyl, halogen, lower alkyl, or lower alkoxy; R represents hydrogen or straight chain lower alkyl of 1 to 4 carbon atoms inclusive such as methyl, ethyl, propyl and n-butyl.

It is to be understood that by the term "halogen" as used throughout the instant diclosure and claims, it is intended to connote all four halogens; i.e., chlorine, bromine, iodine and fluorine. It is to be understood that by the terms "lower alkyl" and "lower alkoxy" as used throughout the instant disclosure and claims, it is intended that the carbon chain which comprises these groups include both straight and branched chain carbon radicals of 1 to 4 carbon atoms inclusive. Exemplary of these carbon chain radicals are methyl, ethyl, propyl, isopropyl, 1-butyl, 1-methylpropyl, 2-methylpropyl, and tert.-butyl.

It will be apparent to those skilled in the art that compounds of Formula I can exist as stereoisomeric modifications when an asymmetric center is present. For example, in the case of a compound of Formula I wherein the "bis-pyrrolinyl moiety" contains an R-substituent other than hydrogen, such as 2-methoxy-10-[5-methyl-1-(5-methyl-1-pyrrolin-2-yl)-2-pyrrolin-2-yl]phenothiazine, two asymmetric centers are present resulting in two racemic modifications. It is possible to separate the racemic modifications into individual (±)-pairs on the basis of the physico-chemical differences such as solubility. The (±)-pairs can be resolved according to conventional procedures by using appropriate optically active acids. It is to be understood that all stereoisomeric forms of the compounds of Formula I are considered to be within the purview of this invention.

The amidine compounds of the present invention characterized by Formula I are obtained by:

Reacting a compound selected from the group consisting of a phenothiazine, acridan, or phenoxazine of the formula

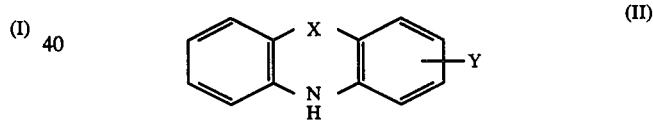

With a pyrrolidinone of the formula

wherein R, X and Y have the same meaning as previously defined in the presence of phosphorus oxychloride in an inert solvent or reacting said phenothiazine, acridan, or phenoxazine with 2-chloro-1-(1-pyrrolin-2-yl)-2-pyrroline hydrochloride in an inert solvent and thereafter, if desired, converting the amidine products in free base form into acid addition salts by reaction with inorganic or organic acids.

Illustrative of suitable phenothiazine reactants which may be employed are:

phenothiazine,
2-chlorophenothiazine,
4-chlorophenothiazine,
2-bromophenothiazine,
2-fluorophenothiazine,
2-iodophenothiazine, 2-trifluoromethylphenothiazine,
4-trifluoromethylphenothiazine
2-methoxyphenothiazine,
4-methoxyphenothiazine,
2-ethoxyphenothiazine,
2-n-propoxyphenothiazine,
2-isopropoxyphenothiazine,
2-n-butoxyphenothiazine,
2-isobutoxyphenothiazine,
2-sec.-butoxyphenothiazine,
4-n-butoxyphenothiazine,
2-methylphenothiazine,
4-methylphenothiazine,
2-isopropylphenothiazine,
2-methylphenothiazine,
2-n-butylphenothiazine,
4-methylphenothiazine,
4-isopropylphenothiazine.

Suitable acridan reactants are:

acridan,
2-methoxyacridan,
4-methoxyacridan,
2-chloroacridan,
4-chloroacridan,
2-trifluoromethylacridan,
4-trifluoromethylacridan,
9,9-dimethylacridan,
2-chloro-9,9-dimethylacridan,
2-trifluoromethyl-9,9-dimethylacridan,
4-methoxy-9,9-dimethylacridan,
2-methylacridan,
4-methylacridan,
4-n-butylacridan,
2-trifluoromethyl-9-methylacridan,
9-ethyl-9-methylacridan,
9,9-di-n-butylacridan.

Suitable phenoxazines are:

phenoxazine,
2-methoxyphenoxazine,
4-methoxyphenoxazine,
4-isopropoxyphenoxazine,
2-methylphenoxazine,
4-methylphenoxazine,
4-n-butylphenoxazine,
2-chlorophenoxazine,
3-chlorophenoxazine,
4-chlorophenoxazine,
2-trifluoromethylphenoxazine.

Suitable pyrrolidinones are:

2-pyrrolidinone,
5-methyl-2-pyrrolidinone,
5-ethyl-2-pyrrolidinone,
5-n-propyl-2-pyrrolidinone,
5n-butyl-2-pyrrolidinone.

The compounds of Formula I are basic and generally crystalline compounds which are practically insoluble in water, but are readily soluble in most organic solvents and in aqueous solutions of organic or inorganic acids.

The compounds characterized by Formula I can be converted, if desired, to corresponding non-toxic pharmaceutically acceptable acid addition salts by admixture of the free base with a selected acid in an inert organic solvent such as ethanol, benzene, ethyl acetate, ether, halogenated hydrocarbons, and the like. A preferred method of salt preparation is to treat the base with substantially one chemical equivalent of an acid such as hydrogen chloride in ethanol solution. The salt precipitates from the ethanolic solution upon chilling or the addition of ether. It is to be understood that both the free base and salt forms of the products of Formula I are useful for the purpose of the invention although salts are, in some instances, particularly preferred because of their increased water solubility.

It is to be understood that the term "non-toxic pharmaceutically acceptable acid addition salt", as used throughout the instant disclosure and the claims, is construed to mean the salt form of an amidine base of the present invention and an inorganic or organic acid which exhibits no significant toxicity when administered at the effective dose for the purpose intended. Some examples of inorganic or organic acids which may be employed to provide a non-toxic pharmaceutically acceptable acid addition salt of the compounds of Formula I are: sulfuric, phosphoric, hydrochloric, hydrobromic, hydroiodic, sulfamic, acetic, latic, maleic, succinic, malic, fumaric, tartaric, citric, gluconic, glutaric, ascorbic, benzoic, cinnamic, isethionic, and related acids.

The free base compounds of Formula I can be prepared by neutralization of the acid addition salt in aqueous base. In a convenient procedure, the salt is mixed with excess sodium hydroxide in aqueous solution, after which the free base can be separated by extraction with a chlorinated hydrocarbon or ether solvent. The solvent can be removed by conventional methods such as evaporation or distillation and the free base compound can be purified by methods such as recrystallization or "short path" distillation at reduced pressures.

In carrying out the process of the invention for the preparation of the bis-pyrrolinyl compounds characterized by Formula I, a phenothiazine base, or an acridan base, or a phenoxazine base is reacted with the R-pyrrolidinone and phosphorus oxychloride in an inert aprotic solvent. Generally, ratios of from 1 to 2 moles of the pyrrolidinone reactant to 1 mole of phosphorus oxychloride and 1 mole of the phenothiazine, acridan or phenoxazine base are employed. A preferred solvent for carrying out the process is 1,2-dichloroethane although other solvents are suitable such as benzene, chloroform, carbon tetrachloride, 1,1-dichloroethane, hexane, xylene, and the like. The process may be carried out at a temperature of about 0° C. to 150° C. but we generally prefer room temperature in the range of about 25°–35° C. In some instances, the reaction mixture is permitted to stand for several days but generally the reaction is essentially complete in about 15 hr.

Whenever compounds characterized by Formula I wherein R is limited to hydrogen are prepared, an alternate aspect of the process of the present invention comprises reaction of a phenothiazine, acridan, or phenoxazine base with the imidoyl chloride "2-chloro-1-(1-pyrrolin-2-yl)-2-pyrroline hydrochloride" in an inert solvent such as 1,2-dichloroethane. Alkylation of the phenothiazine, acridan, or phenoxazine base with 2-chloro-1-(1-pyrrolin-2-yl)pyrroline hydrochloride is preferably carried out in 1,2-dichloroethane at reflux temperature.

According to the foregoing process wherein a phenothiazine, acridan, or phenoxazine base is reacted with a pyrrolidinone and phosphorus oxychloride, monomeric pyrrolinyl compounds described in our co-pending U.S. patent application Ser. No. 147,667 (U.S. Pat. No. 3,719,671) are also obtained, in addition to the bis-pyrrolinyl compounds of Formula I. For example, reaction of phenothiazine, 2-pyrrolidinone, and phosphorus oxychloride in 1,2-dichloroethane provides the bis-pyrrolinyl phenothiazine compounds of the present invention, "10-[1-(1-pyrrolin-2-yl)-2-pyrrolin-2-yl]phenothiazine" and the monomeric pyrrolinyl derivative "10-[2-(1-pyrrolinyl)]phenothiazine" described in co-pending U.S. patent application Ser. No. (U.S. Pat. No. 3,719,671). Separation of the bis-pyrrolinyl derivatives of the present invention from the monomeric pyrrolinyl by-products is generally effected by washing with a solvent, preferably acetone, wherein the bis-pyrrolinyl derivatives of the present invention are relatively less soluble than the monomeric pyrrolinyl by-products or by distillation.

The bis-pyrrolinyl compounds of the present invention are new chemical substances which have useful pharmacological properties. More particularly, they exert an intestinal relaxant effect similar to that obtained with papaverine. Aside from the intestinal relaxant activity, the bis-pyrrolinyl compounds of Formula I have antithrombogenic properties as demonstrated by their ability to inhibit platelet aggregation caused by the addition of adenosine diphosphate to platelet rich plasma.

Intestinal relaxant activity of the bis-pyrrolinyl compounds of the present invention can be measured in standard and accepted in vitro and in vivo pharmacological tests. One such test is carried out essentially as follows. A segment of rabbit ileum is suspended in oxygenated Tyrode's solution and affixed to a tension transducer for electronic recording of isometric contractions. After control responses to a standard dose of a spasmogen such as barium chloride (0.25 mg./ml.) or acetylcholine chloride (1.0 mcg./ml.) are established, the bis-pyrrolinyl compound is added and the response to the spasmogen in the presence of the test compound, again determined. Test compound effect is measured as the percentage reduction in the response to the spasmogen in the presence of the test compound, from the mean control response. The data are expressed in log dose response curves obtained from a minimum of three trials at each of 2 to 5 different concentrations of the test compound. Estimates are made therefrom of the $EC_{50}$ or $ED_{75}$ (concentration causing 50% to 75% reduction respectively in the response of the tissue to the spasmogen).

Papaverine, which is a well-known smooth muscle relaxant, has an $EC_{50}$ of 12.2 mcg./ml. in this test against barium chloride spasms. In general, the bis-pyrrolinyl substances of Formula I are more potent than papaverine. As might be expected, certain of the compounds are more active than others. In this respect, there can be mentioned by way of example 9,9-dimethyl-10-[5-methyl-1-(5-methyl-1-pyrrolin-2-yl)-2-pyrrolin-2-yl]acridan hydrochloride, 10-[1-(1-pyrrolin-2-yl)-2-pyrrolin-2-yl]phenoxazine and 2-methoxy-10-[5-methyl-1-(5-methyl-1-pyrrolin-2-yl)-2-pyrrolin-2-yl]phenothiazine hydrochloride which are 7.6, 3.1 and 1.7 respectively times as potent as papaverine as particularly preferred bis-pyrrolinyl compounds of the present invention.

Apart from intestinal relaxant activity, a bis-pyrrolinyl compound of this invention present in an effective amount in the mammalian circulatory system has the added benefit of providing a protective antithrombogenic effect. Measurement of the antithrombogenic activity of the bis-pyrrolinyl compounds of Formula I can be carried out in a standard pharmacological test which essentially has been described by Born, Nature, 194, 927 (1962) and O'Brien, J. Clin. Path., 15, 446 (1962). This test is a nephelometric method in which the change in turbidity of a specimen of platelet rich blood plasma (generally human blood plasma) is measured on causation of platelet aggregation by addition of a thrombogenic inducing agent such as adenosine diphosphate or collagen. The compounds of the present invention are effective antithrombogenic agents according to this test at concentrations in the order of about 3 to 150 mcg./0.5 ml. human platelet rich plasma. The antithrombogenic effect is measured in the intact animal by applying the foregoing test to blood samples withdrawn prior to and after administration of a bis-pyrrolinyl compound of the present invention to the test animal.

While compounds of Formula I generally exhibit signficant antithrombogenic activity, compounds which reduce the thrombogenic capacity of collagen or adenosine disphosphate induced platelet aggregation by 50% or more at concentrations of less than 15 mcg./0.5 ml. of platelet rich plasma are preferred and by way of example there can be mentioned:

9,9-dimethyl-10-[1-(1-pyrrolin-2-yl)-2-pyrrolin-2-yl]acridan;
9,9-dimethyl-10-[5-methyl-1-(5-methyl-1-pyrrolin-2-yl)-2-pyrrolin-2-yl]acridan;
10-[5-methyl-1-(5-methyl-1-pyrrolin-2-yl)-2-pyrrolin-2-yl]phenothiazine; p0 2-methoxy-10-[5-methyl-1-(5-methyl-1-(pyrrolin-2-yl)-2-pyrrolin-2-yl]phenothiazine;
10-[1-(1-pyrrolin-2-yl)-2-pyrrolin-2-yl]phenoxazine.

In addition to having intestinal relaxant and antithrombogenic properties, compounds of Formula I are effective diuretic agents as demonstrated by the method of W. L. Lipschitz, et al., J. Pharmacol. Expt. Therap., 79, 97 (1943). In this method, groups of 8 rats are fasted 18 hours prior to the experiment. A control group is hydrated orally with 25 ml. per kilogram of body weight of isotonic saline solution which is also the vehicle used for dosing the test compound. One control group received a dose of 960 mg./kg. of body weight of urea. Animals of other groups are treated with various doses of the test compound. Immediately after treatment, the animals are placed in a metabolism cages (two rats of the same group per cage) and maintained without food or water for 5 hrs. The volume of urine excreted by each pair is determined after this period and the pooled urine is analyzed for sodium, potassium, and chloride ions. The results for the test compounds are expressed as ratios of the volume of urine or total quantities of electrolytes (i.e., sodium, potassium, and chloride) excreted during the experimental period compared to the saline and/or urea control group. The test compounds are orally administered in doses ranging from 2.7 to 25 mg./kg. of body weight. In this test, $Ed_{100}$ values (dose providing a 100% increases in volume) for 9,9-dimethyl-10-[5-methyl-1-(5-methyl-1-pyrrolin-2-yl)-2-pyrrolin-2-yl]acridan and 10-[5-methyl-1-(5-methyl-1-pyrrolin-2-yl)-2-pyrrolin-2-yl]-2-(trifluoromethyl)-phenothiazine are 3.58 and 6.63 mg./kg. body weight respectively.

Bis-pyrrolinyl compounds of Formula I and non-toxic pharmaceutically acceptable salts thereof may be administered to mammals by either the parenteral or oral route. Pharmacological activity including diuretic, antithrombogenic, and intestinal relaxant effects are obtained at non-toxic effective doses of the compounds of Formula I ranging from about 0.01 to 30 mg./kg. body weight. With respect to total daily dose, optimum intestinal relaxant and antithrombogenic effects are obtained by oral administration of the bis-pyrrolinyl compounds of Formula I in a non-toxic effective dose ranging from about 0.05 to 100 mg./kg. body weight. It is to be understood that the term "non-toxic effective dose" as used herein refers to the quantity of active ingredient necessary to produce the desired therapeutic effect without causing any significant harmful or deleterious side effects. The process of the present invention for exerting a pharmacological effect in a mammal comprises administering to said mammal a non-toxic effective dose of from 0.01 to 30 mg./kg. body weight of a bis-pyrrolinyl compound of Formula I or a pharmaceutically acceptable acid addition salt thereof to produce an effect selected from the group consisting of diuretic, antithrombogenic and smooth muscle relaxant therein.

Oral toxicity values ($ALD_{50}$) of the substances of Formula I in mice range from about 125 to greater than 1000 milligrams per kilogram of body weight. For instance, the $ALD_{50}$ for 10-[1-(1-pyrrolin-2-yl)-2-pyrrolin-2-yl]phenoxazine hydrochloride is 250–500 mg./kg. body weight.

The compounds of the present invention can be formulated according to conventional pharmaceutical practice to provide pharmaceutical compositions of unit dosage form which may include, for example, tablets, pills, capsules, powders, granules, emulsions, suspensions, and the like. The solid preparations contain the active ingredient in admixture with non-toxic pharmaceutical excipients such as inert diluents, for example calcium carbonate, sodium carbonate, lactose, calcium phosphate or sodium phosphate; granulating and disintegrating agents, for example maize, starch or alginic acid; binding agents, for example starch, gelatin or acacia; and lubricating agents, for example magnesium stearate, stearic acid or talc. The tablets may be uncoated or they may be coated by known techniques so as to defy disintegration and absorption in the gastrointestinal tract and thereby provide a sustained action over a longer period.

Liquid preparations suitable for parenteral administration include solutions, suspensions, or emulsions of the compounds of Formula I. The aqueous suspensions of the pharmaceutical dosage forms of the compounds of Formula I contain the active ingredient in admixture with one or more non-toxic pharmaceutical excipients known to be suitable in the manufacture of aqueous suspensions. Suitable excipients are, for example, suspending agents such as sodium carboxymethylcellulose, methylcellulose, hydroxypropylmethylcellulose, sodium alginate, polyvinylpyrrolidone, gum tragacanth and gum acacia. Suitable dispersing or wetting agents are naturally occurring phosphatides, for example lecithin, polyoxyethylene stearate.

Non-aqueous suspensions may be formulated by suspending the active ingredient in a vegetable oil, for example arachis oil, olive oil, sesame oil or coconut oil, or in a mineral oil, for example liquid paraffin. The suspensions may contain a thickening agent such as bees wax, hard paraffin or cetyl alcohol. Sweetening and flavoring agents generally used in pharmaceutical compositions may also be included such as saccharin, sodium cyclamate, sugar and caramel to provide a palatable oral preparation. The compositions may also contain other additional absorbing agents, stabilizing agents, weighing agents, and buffers.

The following examples further illustrate the present invention and will enable others skilled in the art to understand it more completely. It is to be understood, however, that the invention is not limited solely to the particular examples given below.

In regard to "NMR" data, the following notations are employed: $s$ = singlet, $d$ = doublet, $dd$ = doublet of doublets, $t$ = triplet, $q$ = quintet, $m$ = multiplet, $nm$ = narrow multiplet, $bs$ = broad singlet.

EXAMPLE 1

Phosphorus oxychloride (38.3 g., 0.25 mole) in 50 ml. of 1,2-dichloroethane is added in one portion to a stirred mixture of phenothiazine (49.8 g., 0.25 mole) and 2-pyrrolidinone (42.6 g., 0.5 mole) in 250 ml. of 1,2-dichloroethane. The mixture is stirred for 4 hr. at room temperature, permitted to stand for a period of 15 hr. and then poured into a mixture of 200 ml. of 5N sodium hydroxide and 100 g. of crushed ice. The 1,2-dichloroethane layer is separated and the aqueous layer extracted with 100 ml. of additional 1,2-dichloroethane. The combined 1,2-dichloroethane fractions are sequentially extracted with 300 ml. of 1.5N hydrochloric acid and 200 ml. of water. The combined acid-water extracts are washed with ether, made basic with 5N sodium hydroxide and extracted repeatedly with chloroform. After drying over magnesium sulfate, the chloroform solution is concentrated and the residual material thus obtained stirred with 200 ml. of acetone to remove the acetone soluble 10-[2-(1-pyrrolinyl)]phenothiazine by-product and filtered. The filter cake is washed with additional acetone and dried providing 14.1 g. (17% yield) of 10-[1-1-PYRROLIN-2-YL)-2-PYRROLIN-2-YL]PHENOTHIAZINE as the free base, m.p. 199°–201° C. The bis-pyrrolinyl phenothiazine free base suspended in 60 ml. of absolute ethanol, acidified with an equivalent of ethanolic hydrogen chloride, treated with decolorizing charcoal, filtered, and diluted with 200-250 ml. of anhydrous ether provides the hydrochloride salt. Crystallization of the hydrochloride salt from absolute ethanolanhydrous ether affords analytically pure 10-[1-(1-PYRROLIN-2-YL)-2-PYRROLIN-2-YL PHENOTHIAZINE]HYDROCHLORIDE solvated with 1/5 mole of ethanol as an off white solid, m.p. 237°–239° C. (corr.).

Analysis. Calcd. for $C_{20}H_{19}N_3S \cdot HCl \cdot 1/5\ C_2H_5OH$ (percent): C, 64.63; H, 5.64; Cl, 9.35; N, 11.08. Found (percent): C, 64.68; H, 5.61; Cl, 9.41; N, 11.18.

NMR delta (ppm) ($D_2O$, HDO reference): 1.75m, 2.96m, 3.41m, 4.23m, 5.88nm, 7.0m.

EXAMPLE 2

A solution of 4-chlorophenothiazine (32.3 g., 0.134 mole) and 2-pyrrolidinone (23 g., 0.27 mole) in 125 ml. of 1,2-dichloroethane is added dropwise to a solution of phosphorus oxychloride (20.5 g., 0.134 mole) in 50 ml. of 1,2-dichloroethane in about 35 min. Isolation of the product from the reaction mixture according to the procedure of Example 1 provides 7.5 g., (17.1% yield) of 4-CHLORO-10-[1-(1-PYRROLIN-2-YL)-2-PYRROLIN-2-YL]PHENOTHIAZINE free base, m.p. 195°–197° C. Analytically pure 4-CHLORO-10-[1-(1-

PYRROLIN-2-YL)-2-PYRROLIN-2-YL]PHENO-THIAZINE HYDROCHLORIDE obtained by crystallization from ethanol-ether has a melting point of 232°–234° C. (corr.).

Analysis. Calcd. for $C_{20}H_{18}ClN_3S \cdot HCl$ (percent): C, 59.41; H, 4.74; N, 10.39; Cl, 17.53. Found (percent): C, 59.20; H, 4.74; N, 10.59; Cl, 17.46.

NMR delta (ppm) ($D_2O$, HDO reference): 1.77m, 2.97m, 3.43m, 4.14m, 5.91nm, 6.9m.

EXAMPLE 3

Reaction of 2-methoxyphenothiazine, 2-pyrrolidinone and phosphorus oxychloride in 1,2-dichloroethane according to the procedure of Example 1 affords 2-METHOXY-10-[1-(1-Pyrrolin-2-YL)-2-PYRROLIN-2-YL]PHENOTHIAZINE free base, m.p. 151°–153° C. (corr.), from isopropyl alcohol.

Analysis. Calcd. for $C_{21}H_{21}N_3OS$ (percent): C, 69.39; H, 5.83; N, 11.56. Found (percent): C, 69.35; H, 5.87; N, 11.76.

NMR delta (ppm) ($CDCl_3$, TMS reference): 1.78q (7.0), 2.77m, 3.56t (7.1), 3.71s, 4.19dd (8.0, 9.8), 5.20t (2.8), 6.5m, 6.9m.

EXAMPLE 4

A mixture of 5-methyl-2-pyrrolidinone (6.0 g., 0.06 mole), phosphorus oxychloride (9.2 g., 0.06 mole) in 60 ml. of 1,2-dichloroethane is refluxed for 10 min. A solution of phenothiazine (6.0 g., 0.03 mole) in 20 ml. of 1,2-dichloroethane is added at the end of the reflux period and the reaction mixture stirred and refluxed for 20 hr., and then poured onto 20 ml. of 5N potassium hydroxide and 20 g. of crushed ice. The 1,2-dichloroethane layer is separated and extracted with 30 ml. of 1.5N hydrochloric acid and 30 ml. of water removing water soluble by-product 10-[2-(5-methyl-1-pyrrolinyl)]phenothiazine hydrochloride. After drying the 1,2-dichloroethane solution over magnesium sulfate, the 1,2-dichloroethane solution is concentrated and the solid thus obtained stirred with 40 ml. of acetone and filtered. Crystallization of the filtercake from ethanol-ether provides analytically pure 10-[5-METHYL-1-(5-METHYL-1-PYRROLIN-2-YL)-2-PYRROLIN-2-YL]PHENOTHIAZINE HYDROCHLORIDE in a yield of 17%, m.p. 257°–264° C. (corr.).

Analysis. Calcd. for $C_{22}H_{23}N_3S \cdot HCl$ (percent): C, 66.40; H, 6.08; N, 10.56; Cl, 8.91. Found (percent): C, 66.51; H, 6.14; N, 10.52; Cl, 8.99.

NMR delta (ppm) ($CDCl_3$, TMS reference): 1.41d (6.4), 1.57d (6.2), 1.7–3.5m, 4.05m, 5.62m, 5.86t (2.9), 7.0m, 11.75bs.

EXAMPLE 5

Reaction of 5-methyl-2-pyrrolidinone, 2-methoxyphenothiazine and phosphorus oxychloride in 1,2-dichloroethane according to the procedure of Example 4 affords 2-METHOXY-10-[5-METHYL-1-(5-METHYL-1-PYRROLIN-2-YL)-2-PYRROLIN-2-YL]PHENOTHIAZINE HYDROCHLORIDE (8.6% yield), m.p. 236.5°–238.5° C. (corr.), from ethanol-ether.

Analysis. Calcd. for $C_{23}H_{25}N_3OS \cdot HCl$ (percent): C, 64.54; H, 6.12; N, 9.82; Cl, 8.29. Found (percent): C, 64.50; H, 6.15; N, 9.88; Cl, 8.33.

NMR delta (ppm) $CDCl_3$,TMS reference): 1.38d (6.3), 1.54d (6.4), 1.56d (6.4), 1.6–3.3m, 3.70s, 4.10m, 5.57m, 5.81t (3.0), 6.8m, 11.93bs.

EXAMPLE 6

A mixture of 5-methyl-2-pyrrolidinone (2.0 g., 0.02 mole) and phosphorus oxychloride (3.0 g., 0.02 mole) in 15 ml. of 1,2-dichloroethane after standing 15 hr. at room temperature is combined with 9,9-dimethylacridan (2.1 g., 0.01 mole) after a 48 hr. period is added to 30 ml. of 5N potassium hydroxide and 30 g. of crushed ice. The 1,2-dichloroethane fraction is separated, extracted with 50 ml. of 1.5N hydrochloride acid and 50 ml. of water and dried over magnesium sulfate. Concentration of the 1,2-dichloroethane solution provides a residue which is stirred with 100 ml. of ether and filtered. The filter cake containing crude hydrochloride salt of the product is stirred with sodium hydroxide solution affording the free base. Crystallization from n-heptane provides 1.3 g. (35% yield) of 9,9-DIMETHYL-10-[5-METHYL-1-(5-METHYL-1-PYRROLIN-2-YL)-2-PYRROLIN-2-YL]ACRIDAN, m.p. 135°–139° C. from which the hydrochloride salt is prepared according to the procedure of Example 1. Analytically pure 9,9-DIMETHYL-10-[5-METHYL-1-(5-METHYL-1-PYRROLIN-2-YL)-2-PYRROLIN-2-YL]ACRIDAN HYDROCHLORIDE, from acetone-ether, has a melting point of 247.5°–248.0° C. (corr.).

Analysis. Calcd. for $C_{25}H_{29}N_3 \cdot HCl$ (percent): C, 73.60; H, 7.41; N, 10.30; Cl, 8.69. Found (percent): C, 73.98; H, 7.40; N, 10.22; Cl, 8.67.

NMR delta (ppm) ($CDCl_3$, TMS reference): 1.40d (6.2), 1.45d (6.2), 1.61s, 1.70d (6.2), 1.72s, 1.8–3.2m, 4.16m, 5.69m, 5.82t (2.9), 6.7m, 7.3m, 11.82bs.

EXAMPLE 7

A mixture of acridan (3.6 g., 0.02 mole) and 2-chloro-1-(1-pyrrolin-2-yl)-2-pyrroline hydrochloride (5.1 g., 0.025 mole), obtained according to the method of H. Brederick, et al., Chem. Ber., 94, 2292 (1961), in 50 ml. of 1,2-dichloroethane is refluxed for a period of 15 hr. The mixture is sequentially extracted with 50 ml. of 1.5N hydrochloric acid and three 50 ml. portions of water. The combined acid-water extracts are basified with 5N potassium hydroxide, extracted with ether and the ethereal extract concentrated. Crystallization of the residue thus obtained from ethanol affords the free base 10-[1-1-PYRROLIN-2-YL)-2-PYRROLIN-2-YL]ACRIDAN, m.p. 179°–181° C. which is converted according to the procedure of Example 1 to 10-[1-(1-PYRROLIN-2-YL)-2-PYRROLIN-2-YL]ACRIDAN HYDROCHLORIDE, m.p. 212.5°–216.5° C. (dec.) (corr.)., from ethanol-ether.

Analysis. Calcd. for $C_{21}H_{21}N_2 \cdot HCl$ (percent): C, 71.68; H, 6.30; N, 11.94; Cl, 10.08. Found (percent): C, 71.43; H, 6.24; N, 11.90; Cl, 9.85.

NMR delta (ppm) ($D_2O$, HDO reference): 1.60m, 2.33m, 2.80m, 3.36m, 3.69s, 4.11m, 5.49nm, 6.9m.

EXAMPLE 8

Reaction of 9,9-dimethylacridan, and 2-chloro-1-(1-pyrrolin-2-yl)-2-pyrroline hydrochloride according to the procedure of Example 7 affords a 21% yield of the free base, 9,9-DIMETHYL-10-[1-(1-PYRROLIN-2-YL)-2-PYRROLIN-2-YL]ACRIDAN, m.p. 166°–168° C. Acidification of the free base with ethanolic hydrogen chloride according to the procedure of Example 1 provides 9,9-DIMETHYL-10-[1-(1-PYRROLIN-2-YL)-2-PYRROLIN-2-YL]ACRIDAN HYDROCHLORIDE, m.p. 256.5°–258° C. (dec.) (corr.), from benzene-ether.

Analysis. Calcd. for $C_{23}H_{25}N_3 \cdot HCl$ (percent): C, 72.71; H, 6.90; N, 11.06; Cl, 9.33. Found (percent): C, 72.46; H, 6.82; N, 10.88; Cl, 9.04.

NMR delta (ppm) CDCl$_3$, TMS reference): 1.61s, 1.73s, 1.90m, 2.29m, 3.07m, 3.72t (7.0), 4.80dd (8.0, 8.5), 5.88t (3.0), 6.7m, 7.3m.

EXAMPLE 9

Reaction of phenoxazine with 2-chloro-1-(1-pyrrolin-2-yl)pyrrolin hydrochloride according to the procedure of Example 7 affords 10-[1-(1-PYRROLIN-2-YL)-2-PYRROLIN-2-YL]PHENOXAZINE HYDROCHLORIDE, m.p. 257.5°–263° C. (corr.), from ethanol-ether.

Analysis. Calcd. for $C_{20}H_{19}N_3O \cdot HCl$ (percent): C, 97.88; H, 5.70; N, 11.88; Cl, 10.02. Found (percent): C, 67.52; H, 5.82; N, 11.83; Cl, 9.85.

NMR delta (ppm) (CDCl$_3$, TMS reference): 2.08m, 2.95m, 3.72t (7.1), 4.65dd (8.0, 8.5), 5.86t (2.9), 6.4m, 6.8m.

EXAMPLE 10

Reaction of 2-chlorophenoxazine with 2-chloro-(1-pyrrolin-2-yl)pyrroline hydrochloride according to the procedure of Example 7 affords 2-CHLORO-10-[1-(1-PYRROLIN-2-YL)-2-PYRROLIN-2-YL]PHENOXAZINE HYDROCHLORIDE, m.p. 262.5°–264.5° C. (dec.) (corr.), from ethanol-ether.

Analysis. Calcd. for $C_{20}H_{18}ClN_3O \cdot HCl$ (percent): C, 61.86; H, 4.93; N, 10.82; Cl, 18.27. Found (percent): C, 61.65; H, 4.97; N, 10.79; Cl, 18.16.

NMR delta (ppm) (CDCl$_3$, TMS reference): 2.17m, 2.98m, 3.74t (7.0), 4.68dd (8.0, 9.0), 5.88t (3.0), 6.4m, 6.8m, 12.0bs.

EXAMPLE 11

Reaction of 2-trifluoromethylphenoxazine with 2-chloro-1-(1-pyrrolin-2-yl)pyrroline hydrochloride according to the procedure of Example 7 affords the free base, 2-TRIFLUOROMETHYL-10-[1-(1-PYRROLIN-2-YL)-2-PYRROLIN-2-YL]PHENOXAZINE, m.p. 140°–142° C., from n-hexane. Conversion of the free base affords 2-TRIFLUOROMETHYL-10[1-(1-PYRROLIN-2-YL)-2-PYRROLIN-2-YL]PHENOXAZINE HYDROCHLORIDE HYDRATE, m.p. 222.5°–229° C. (dec.) (corr.).

Analysis. Calcd. for $C_{12}H_{18}F_3N_3 \cdot HCl \cdot H_2O$ (percent): C, 57.35; H, 4.81; N, 9.55; Cl, 8.06. Found (percent): C, 57.42; H, 4.78; N, 9.43; Cl, 8.32.

NMR delta (ppm) (CDCl$_3$, TMS reference): 2.13m, 2.98m, 3.75t (7.0), 4.67dd (9.0, 8.0), 5.90t (3.0), 6.5m, 6.8m, 11.63bs.

EXAMPLE 12

Reaction of 3-chlorophenoxazine with 2-chloro-(1-pyrrolin-;b 2-yl)pyrroline hydrochloride according to the procedure of Example 7 affords 3-CHLORO-10-[1-(1-PYRROLIN-2-YL)-2-PYRROLIN-2-YL]PHENOXAZINE HYDROCHLORIDE, m.p. 262.5°–270° C. (dec.) (corr.), from ethanol-ether.

Analysis. Calcd. for $C_{20}H_{18}ClN_3O \cdot HCl$ (percent): C, 61.86; H, 4.93; N, 10.82; Cl, 18.27. Found (percent): C, 61.82; H, 4.99; N, 10.74; Cl, 18.03.

NMR delta (ppm) (CDCl$_3$, TMS reference): 2.12m, 2.97m, 3.73t (7.0), 4.67dd (9.0, 8.0), 5.87t (3.0), 6.4m, 6.8m.

EXAMPLE 13

Reaction of 4-chlorophenoxazine with 2-chloro-(1-pyrrolin-2-yl)pyrroline hydrochloride according to the procedure of Example 7 affords 4-CHLORO-10-[1-(1-PYRROLIN-2-PYRROLIN-2-YL]PHENOXAZINE HYDROCHLORIDE, m.p. 278°282° C. (dec.), from ethanol-ether.

Analysis. Calcd. for $C_{20}H_{18}ClN_3O \cdot HCl$ (percent): C, 61.86; H, 4.93; N, 10.82; Cl, 18.27. Found (percent): C, 61.87; H, 4.99; N, 10.82; Cl, 18.16.

NMR delta (ppm) (CDCl$_3$, TMS reference): 2.11m, 2.97m, 3.74t (7.0), 4.67dd (9.0, 8.0), 5.87t (3.0), 6.4m, 6.8m.

EXAMPLE 14

Reaction of the phenoxazines:

2-methoxyphenoxazine,
4-methoxyphenoxazine,
4-isopropoxyphenoxazine,
2-methylphenoxazine,
4-methylphenoxazine,
4-n-butylphenoxazine with 2-chloro-1-(1-pyrrolin-2-yl)pyrroline hydrochloride according to the procedure of Example 7 provides the respective bis-pyrrolinyl phenoxazines:

2-METHOXY-10-[1-(1-PYRROLIN-2-YL)-2-PYRROLIN-2-YL]PHENOXAZINE HYDROCHLORIDE, m.p. 201.5°–206.5° C. (dec.)(corr.). Analysis. Calcd. for $C_{21}H_{21}N_3O_2 \cdot HCl$ (percent): C, 65.70; H, 5.78; N, 10.95; Cl, 9.24. Found (percent): C, 64.98; H, 5.71; N, 11.04; Cl, 9.23. NMR delta (ppm) (CDCl$_3$, TMS reference): 2.10m, 3.01m, 3.72t (7.1), 3.71s, 4.63t (7.5), 5.9–6.9m.

4-METHOXY-10-[1-(1-PYRROLIN-2-YL)-2-PYRROLIN-2-YL]PHENOXAZINE,

4-ISOPROPOXY-10-[1-(1-PYRROLIN-2-YL)-2-PYRROLIN-2-YL]PHENOXAZINE,

2-METHYL-10-[1-(1-PYRROLIN-2-YL)-2-PYRROLIN-2-YL]PHENOXAZINE,

4-METHYL-10-[1-(1-PYRROLIN-2-YL)-2-PYRROLIN-2-YL]PHENOXAZINE, 4-n-BUTYL-10-[1-(1-PYRROLIN-2-YL)-2-PYRROLIN-2-YL]PHENOXAZINE.

EXAMPLE 15

Reaction of phenoxazine with 5-methyl-2-pyrrolidinone or 5-n-butyl-2-pyrrolidinone according to the procedure of Example 4 provides the bis-pyrrolinyl phenoxazines:

10-[5-METHYL-1-(5-METHYL-1-PYRROLIN-2-YL)-2-PYRROLIN-2-YL]PHENOXAZINE,

10-[5-n-BUTYL-1-(5-n-BUTYL-1-PYROLLIN-2-YL)-2-PYRROLIN-2-YL]PHENOXAZINE.

Reaction of 4-chlorophenoxazine with 5-methyl-2-pyrrolidinone according to the procedure of Example 4 provides

4-CHLORO-10-[5-METHYL-1-(5-METHYL-1-PYRROLIN-2-YL)-2-PYRROLIN-2-YL]PHENOXAZINE.

EXAMPLE 16

Reaction of the phenothiazines:

2-trifluorophenothiazine,
2-chlorophenothiazine,
3-chlorophenothiazine,
4-isopropoxyphenothiazine,
2-methylphenothiazine,
2-n-butylphenothiazine,
4-methylphenothiazine,
4-isopropylphenothiazine with 2-chloro-1-(1-pyrrolin-2-yl)pyrroline hydrochloride according to the procedure of Example 7 provides the respective bis-pyrrolinyl phenothiazines:

2-TRIFLUOROMETHYL-10-[1-(1-PYRROLIN-2-YL)-2-PYRROLIN-2-YL]PHENOTHIAZINE,
2-CHLORO-10-[1-(1-PYRROLIN-2-YL)-2-PYRROLIN-2-YL]PHENOTHIAZINE,
3-CHLORO-10-[1-(1-PYRROLIN-2-YL)-2-PYRROLIN-2-YL]PHENOTHIAZINE,
4-ISOPROPOXY-10-[1-(1-PYRROLIN-2-YL)-2-PYRROLIN-2-YL]PHENOTHIAZINE,
2-METHYL-10-[1-(1-PYRROLIN-2-YL)-2-PYRROLIN-2-YL]PHENOTHIAZINE,
2-n-BUTYL-10-[1-(1-PYRROLIN-2-YL)-2-PYRROLIN-2-YL]PHENOTHIAZINE,
4-METHYL-10-[1-(1-PYRROLIN-2-YL)-2-PYRROLIN-2-YL]PHENOTHIAZINE,
4-ISOPROPYL-10-[1-(1-PYRROLIN-2-YL)-2-PYRROLIN-2-YL]PHENOTHIAZINE.

EXAMPLE 17

Reaction of phenothiazine with 5-n-butyl-2-pyrrolidinone according to the procedure of Example 4 provides 10-[5-n-BUTYL-1-(5-n-BUTYL-1-PYRROLIN-2-YL)-2-PYRROLIN-2-YL]PHENOTHIAZINE.

EXAMPLE 18

Reaction of the acridans:

2-chloroacridan,
4-methoxyacridan,
4-isopropoxyacridan, 4-trifluoromethylacridan,
2-methylacridan, 4-methylacridan,
4-n-butylacridan,
2-trifluoromethyl-9,9-dimethylacridan,
2-trifluoromethyl-9-methylacridan,
2-chloro-9,9-dimethylacridan,
9-ethyl-9-methylacridan,
9,9-di-n-butylacridan with 2-chloro-1-(1-pyrrolin-2-yl)pyrroline hydrochloride according to the procedure of Example 7 provides the respective bis-pyrrolinyl acridans:

2-CHLORO-10-[1-(1-PYRROLIN-2-YL)-2-PYRROLIN-2-YL]ACRIDAN,
4-METHOXY-10-[1-(1-PYRROLIN-2-YL)-2-PYRROLIN-2-YL]ACRIDAN,
4-ISOPROPOXY-10-[1-(1-PYRROLIN-2-YL)-2-PYRROLIN-2-YL]ACRIDAN,
4-TRIFLUOROMETHYL-10-[1-(1-PYRROLIN-2-YL)-2-PYRROLIN-2-YL]ACRIDAN,
2-METHYL-10-[1-(1-PYRROLIN-2-YL)-2-PYRROLIN-2-YL]ACRIDAN,
4-METHYL-10-[1-(1-PYRROLIN-2-YL)-2-PYRROLIN-2-YL]ACRIDAN,
4-n-BUTYL-10-[1-(1-PYRROLIN-2-YL)-2-PYRROLIN-2-YL]ACRIDAN,
2-TRIFLUOROMETHYL-9,9-DIMETHYL-10-[1-(1-PYRROLIN-2-YL)-2-PYRROLIN-2-YL]ACRIDAN,
2-TRIFLUOROMETHYL-9-METHYL-10-[1-(1-PYRROLIN-2-YL)-2-PYRROLIN-2-YL]ACRIDAN,
2-CHLORO-9,9-DIMETHYL-10-[1-(1-PYRROLIN-2-YL)-2-PYRROLIN-2-YL]ACRIDAN,
9-ETHYL-9-METHYL-10-[1-(1-PYRROLIN-2-YL)-2-PYRROLIN-2-YL]ACRIDAN,
9,9-DI-n-BUTYL-10-[1-(1-PYRROLIN-2-YL)-2-PYRROLIN-2-YL]ACRIDAN.

EXAMPLE 19

Reaction of acridan and 2-chloroacridan with 5-methyl-2-pyrrolidinone and 5-n-butyl-2-pyrrolidinone respectively according to the procedure of Example 4 provides:

2-CHLORO-10-[5-METHYL-1-(5-METHYL-1-PYRROLIN-2-YL)-2-PYRROLIN-2-YL]ACRIDAN,
10-[5-n-BUTYL-1-(5-n-BUTYL-1-PYRROLIN-2-YL)-2-PYRROLIN-2-YL]ACRIDAN.

EXAMPLE 20

A solution of 5-methyl-2-pyrrolidinone (19.8 g., 0.2 mole) in 25 ml. of xylene is added drop-wise to a mixture of 2-trifluoromethylphenothiazine (26.7 g., 0.1 mole) and phosphorus oxychloride (15.3 g., 0.1 mole) in 125 ml. of refluxing xylene in a 2 hour period. When the addition is complete, refluxing is continued for an additional 1.5 hr., the reaction mixture poured into 75 ml. of 5 N sodium hydroxide and 75 g. of crushed ice, and, after mixing well, the xylene fraction is separated. The xylene fraction is sequentially extracted with 100 ml. of 1.5 HCl followed by 100 ml. of water and then made basic by stirring with 5 N sodium hydroxide solution. Separation of the basified xylene fraction which is dried over magnesium sulfate and concentrated under reduced pressure provides a residue which is taken up in 50 ml. of benzene and the solution then concentrated. An additional 100 ml. portion of benzene is added to the residue thus obtained and the solution partially concentrated until crystals begin to form. After cooling and standing, the mixture is filtered to remove recovered 2-trifluoromethylphenothiazine starting material. Concentration of the filtrate affords a residual material which is taken up in ether, extracted with 1.5 N hydrochloric acid and then with 50 ml. of water. The combined acid-aqueous extracts are made basic with sodium hydroxide and the mixture extracted with ether. The ethereal extract is dried over magnesium sulfate, filtered, and concentrated. Distillation of the residual oil through a 6 cm. column provides 10-[5-methyl-1-(5-methyl-1-pyrrolin-2-yl)-2-pyrrolin-2-yl]-2-(trifluoromethyl)phenothiazine free base, b.p. 175°–185° C./0.15 mm. Hg. The bis-pyrrolinyl phenothiazine free base is taken up in ethanol and acidified with ethanolic hydrogen chloride. Addition of ether provides the hydrochloride salt which crystallized from ethanol affords analytically pure 10-[5-METHYL-1-(5-METHYL-1-PYRROLIN-2-YL)-2-PYRROLIN-2-YL]-2-(TRIFLUOROMETHYL)PHENOTHIAZINE HYDROCHLORIDE, m.p. 250°–253° C. (dec.)(corr.).

Analysis. Calcd. for $C_{23}H_{22}F_3N_3S \cdot HCl$: C, 59.28; H, 4.98; N, 9.02; Cl, 7.61. Found: C, 59.18; H, 5.14; N, 9.05; Cl, 7.39.

NMR delta (ppm)(CDCl$_3$, TMS reference): 1.49d (6.5), 1.55d (6.5), 2.37m, 3.12m, 4.03m, 5.50m, 5.94m, 7.05m, 11.8bs.

EXAMPLE 21

Pharmaceutical Compositions

The bis-pyrrolinyl compounds of the present invention characterized by Formula I are compounded with pharmacologically acceptable carriers to provide compositions useful in the present invention. Typical of the pharmaceutical compositions are the following:

A. Tablets — The bis-pyrrolinyl compounds of Formula I are compounded into tablets according to the following example:

| Materials | Amount |
|---|---|
| 9,9-Dimethyl-10-[5-methyl-1-(5-methyl-1-pyrrolin-2-yl)-2-pyrrolin-2-yl]acridan hydrochloride | 54.9 g. |
| Magnesium stearate | 1.3 g. |
| Corn starch | 12.4 g. |
| Corn starch, pregelatinized | 1.3 g. |
| Lactose | 181.0 g. |

The foregoing materials are blended in a twin-shell blender and then granulated and pressed into tablets employing 250 mg. each. Each tablet contains about 50 mg. of active ingredient. The tablet may be scored and quartered so that unit dose of 12.5 mg. of active ingredient may be conveniently obtained.

B. Capsules — The bis-pyrrolinyl compounds of Formula I are compounded into capsules according to the following example:

| Materials | Amount |
|---|---|
| Active ingredient | 125.0 mg. |
| Lactose | 146.0 mg. |
| Magnesium stearate | 4.0 g. |

The foregoing materials are blended in a twin-shell blender and then filled into No. 1 hard gelatin capsules. Each capsule contains 125 g. of active ingredient.

C. Solution for oral or parenteral administration — A sterile aqueous solution having a concentration of 40 mg. per ml. of 9,9-dimethyl-10-[5-methyl-1-(5-methyl-1-pyrrolin-2-yl)-2-pyrrolin-2-yl]acridan hydrochloride is prepared by dissolving 400 g. of the substance in 9 liters of water for injection, U.S.P., adjusting the pH to 5.5 with dilute aqueous sodium hydroxide and dilution to 10 liters. This solution is then filtered sparkling clear and filled into 2 ml. glass ampoules and sealed.

While specific embodiments are disclosed in the foregoing specification, it will be appreciated that other modifications may be made without departing from the spirit and scope of the appended claims.

What is claimed is:

1. A compound selected from the group consisting of 10-(bis-pyrrolinyl)acridans represented by

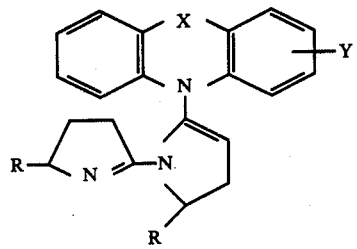

and a non-toxic pharmaceutically acceptable acid addition salt thereof wherein
   X is a divalent methylene radical represented by the formula —C(Z$_1$Z$_3$)—, wherein Z$_1$ and Z$_2$ are independently selected from hydrogen or straight chain lower alkyl of from 1 to 4 carbon atoms inclusive;
   Y represents hydrogen, trifluoromethyl, halogen, lower alkyl of from 1 to 4 carbon atoms inclusive or lower alkoxy of 1 to 4 carbon atoms inclusive; and
   R represents hydrogen or straight chain lower alkyl of 1 to 4 carbon atoms inclusive.

2. A compound according to claim 1 being a member selected from the group consisting of 10-[1-(1-pyrrolin-2-yl)-2-pyrrolin-2-yl]acridan or a pharmaceutically acceptable non-toxic acid addition salt thereof.

3. A compound according to claim 1 being a member selected from the group consisting of 9,9-dimethyl-10-[1-(1-pyrrolin-2-yl)-2-pyrrolin-2-yl]acridan or a pharmaceutically acceptable non-toxic acid addition salt thereof.

4. A compound according to claim 1 being a member selected from the group consisting of 9,9-dimethyl-10-[5-methyl-1-(5-methyl-1-pyrrolin-2-yl)-2-pyrrolin-2-yl]acridan or a pharmaceutically acceptable non-toxic acid addition salt thereof.

* * * * *